United States Patent
Griesbach, III et al.

(10) Patent No.: US 6,576,575 B2
(45) Date of Patent: *Jun. 10, 2003

(54) DISPERSIBLE ADHERENT ARTICLE

(75) Inventors: Henry L. Griesbach, III, Clarkston, GA (US); Julie R. Taylor, Snellville, GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/570,719

(22) Filed: May 15, 2000

(65) Prior Publication Data

US 2003/0073362 A1 Apr. 17, 2003

(51) Int. Cl.$^7$ .......................... B32B 27/12; B32B 15/04; A61E 13/00
(52) U.S. Cl. .................. 442/151; 442/149; 442/151; 442/414; 442/415; 428/343; 602/54; 602/58; 604/304; 604/307; 604/308; 424/443; 424/445
(58) Field of Search ................. 442/149, 151, 442/394, 414, 415, 416; 428/343, 352; 602/41–59; 128/888, 889; 424/443, 445, 448

(56) References Cited

U.S. PATENT DOCUMENTS

| | | |
|---|---|---|
| 3,610,245 A | 10/1971 | Bernardin |
| 3,616,797 A | 11/1971 | Champaigne, Jr. et al. |
| 3,635,221 A | 1/1972 | Chapmaigne, Jr. |
| 3,654,928 A | 4/1972 | Duchane |
| 3,881,210 A | 5/1975 | Drach et al. |
| 4,033,918 A | 7/1977 | Hauber |
| 4,210,633 A | 7/1980 | Takruri et al. |
| 4,258,849 A | 3/1981 | Miller |
| 4,372,311 A | 2/1983 | Potts |

(List continued on next page.)

FOREIGN PATENT DOCUMENTS

| | | |
|---|---|---|
| CA | 2093051 | 6/1994 |
| CA | 2111173 | 2/1995 |
| DE | 3227065 A | 1/1984 |
| EP | 726068 A2 | 8/1996 |
| GB | 2254626 A | 10/1992 |
| GB | 2284820 A | 6/1995 |
| GB | 2295553 A | 6/1996 |
| JP | 274694 | 3/1990 |
| JP | 2082925 | 3/1990 |
| JP | 3076900 A | 4/1991 |
| JP | 3113099 | 5/1991 |
| JP | 5321105 A | 12/1993 |
| JP | 8158224 A | 6/1996 |
| WO | 94/25189 | 11/1994 |
| WO | 96/04077 | 2/1996 |
| WO | WO 97/02375 | * 1/1997 |

OTHER PUBLICATIONS

Int'l Search Report dated Apr. 2, 2002.

Primary Examiner—Terrel Morris
Assistant Examiner—Jenna-Leigh Befumo
(74) Attorney, Agent, or Firm—Dority & Manning, P.A.

(57) ABSTRACT

An adherent article, such as a bandage or adhesive tape, having a nonwoven substrate that contains water soluble fibers is provided. The water soluble fibers of the nonwoven substrate can include polyvinyl alcohol fibers that only dissolve at temperatures greater than 37° C. and/or polyvinyl alcohol fibers that can dissolve at temperatures less than about 37° C. The adherent article also includes a pressure-sensitive adhesive applied to the nonwoven substrate that facilitates adherence of the substrate to human skin. The pressure-sensitive adhesive can be water soluble or generally insoluble, but dispersible in water.

45 Claims, 1 Drawing Sheet

U.S. PATENT DOCUMENTS

| | | |
|---|---|---|
| 4,372,447 A | 2/1983 | Miller |
| 4,575,891 A | 3/1986 | Valente |
| 4,639,390 A | 1/1987 | Shoji |
| 4,990,339 A | 2/1991 | Scholl et al. |
| 4,998,984 A | 3/1991 | McClendon |
| 5,181,966 A | 1/1993 | Honeycutt et al. |
| 5,181,967 A | 1/1993 | Honeycutt |
| 5,207,837 A | 5/1993 | Honeycutt |
| 5,208,104 A | 5/1993 | Ueda et al. |
| 5,252,332 A | 10/1993 | Goldstein |
| 5,256,417 A | 10/1993 | Koltisko |
| 5,264,269 A | 11/1993 | Kakiuchi et al. |
| 5,268,222 A | 12/1993 | Honeycutt |
| 5,281,306 A | 1/1994 | Kakiuchi et al. |
| 5,342,335 A | 8/1994 | Rhim |
| 5,445,785 A | 8/1995 | Rhim |
| 5,470,653 A | 11/1995 | Honeycutt et al. |
| 5,472,518 A | 12/1995 | Patnode et al. |
| 5,486,418 A | 1/1996 | Ohmory et al. |
| 5,500,068 A | 3/1996 | Srinivasan et al. |
| 5,500,281 A | 3/1996 | Srinivasan et al. |
| 5,508,101 A | 4/1996 | Patnode et al. |
| 5,509,913 A | 4/1996 | Yeo |
| 5,512,612 A | 4/1996 | Brown et al. |
| 5,527,845 A | 6/1996 | Strelow et al. |
| 5,567,510 A | 10/1996 | Patnode e tal. |
| 5,599,872 A | 2/1997 | Sulewski |
| 5,620,786 A | 4/1997 | Honeycutt et al. |
| 5,630,972 A | 5/1997 | Patnode et al. |
| 5,641,567 A | 6/1997 | Brown et al. |
| 5,650,219 A | 7/1997 | Honeycutt |
| 5,658,977 A | 8/1997 | Yang et al. |
| 5,665,824 A | 9/1997 | Chang et al. |
| 5,735,812 A | 4/1998 | Hardy |
| 5,763,065 A | 6/1998 | Patnode et al. |
| 5,840,633 A | 11/1998 | Kurihara et al. |
| 5,871,679 A | 2/1999 | Honeycutt |
| 5,916,678 A | 6/1999 | Jackson et al. |
| 5,935,880 A | 8/1999 | Wang et al. |
| 5,947,917 A * | 9/1999 | Carte et al. .................... 602/52 |
| 5,948,710 A | 9/1999 | Pomplun et al. |
| 5,952,251 A | 9/1999 | Jackson et al. |
| 5,952,420 A | 9/1999 | Senkus et al. |
| 5,986,004 A * | 11/1999 | Pomplun et al. ............ 442/152 |
| 6,112,385 A | 9/2000 | Fleissner et al. |
| 6,451,718 B1 | 9/2002 | Yamada et al. |

* cited by examiner

FIGURE 1

DISPERSIBLE ADHERENT ARTICLE

BACKGROUND OF THE INVENTION

Adherent articles, such as bandages or adhesive tapes, are commonly used to cover wounds, cuts, blisters, and the like. Such adherent articles typically include an adhesive material that is applied to a substrate material. To use an adherent article, a user can first position a portion of the substrate material over the relevant wound. Thereafter, the user adheres the substrate material to the surrounding areas of skin using the adhesive applied thereto. The adherence of the substrate material to the skin allows the adherent article to be tightly fitted over the wound to protect the wound from infection.

However, one problem associated with conventional adherent articles relates to the removal of such articles from the skin. In particular, a user must typically forcibly tear the article away from the skin to break the adhesive bond of the substrate to the skin. Such tearing often imparts substantial pain to the user. As such, a need currently exists for an adherent article that can be more easily removed than conventional articles.

SUMMARY OF THE INVENTION

In response to the discussed difficulties and problems encountered in the prior art, a new adherent article has been discovered. In general, an adherent article, such as a bandage or adhesive tape, of the present invention contains water soluble fibers that allow the adherent article to be removed from human skin with an aqueous solution. In one embodiment, an article of the present invention includes a nonwoven substrate made from water soluble polyvinyl alcohol fibers and a generally water insoluble, dispersible pressure-sensitive adhesive.

In accordance with the present invention, any fibers known in the art to substantially dissolve in aqueous solutions at a certain temperature can generally be used as the water soluble fibers of the nonwoven substrate. For example, fibers that can substantially dissolve in an aqueous solution at temperatures below about 37° C., i.e., cold water soluble fibers, can generally be used in a nonwoven substrate of the present invention. In one embodiment, polyvinyl alcohol fibers that can dissolve in water at temperatures between about 20° C. to about 35° C., or greater, are employed. Moreover, fibers that can only substantially dissolve in an aqueous solution at temperatures greater than 37° C., i.e., hot water soluble fibers, can also be used. For example, in some embodiments, polyvinyl alcohol fibers that only dissolve at temperatures of at least 37° C. to about 50° C. can be used in the present invention.

In addition to water soluble fibers, the nonwoven substrate can also include various other components. In particular, any material that does not affect the solubility of the water soluble fibers can be added. In particular, the nonwoven substrate can include fibers that are generally insoluble and dispersible in an aqueous environment. For example, in one embodiment, the nonwoven substrate can include staple fibers, such as rayon fibers. Moreover, in another embodiment, the dispersible fibers can be pulp fibers either alone or in combination with other fibers. By containing pulp fibers, for example, the nonwoven substrate can be disposed of by applying substantial amounts of water thereto. Conventional water sources, such as faucets or shower heads, can be used to dispense water onto the substrate. After applying water to the substrate, the water soluble fibers substantially dissolve into solution and the remaining pulp fibers disperse such that they can be disposed of by conventional water disposal techniques.

In general, a nonwoven substrate of the present invention typically contains at least 50% by weight of water soluble fibers. In particular embodiments, the nonwoven substrate may contain at least about 70% by weight of water soluble fibers, or least about 80% by weight of water soluble fibers. Moreover, regardless of the amount of water soluble fibers present within the substrate, it is also typically desired that the amount of additional components, e.g., pulp fibers, rayon fibers, etc., applied to the nonwoven substrate not exceed about 50% by weight of the substrate.

In accordance with the present invention, the adherent article also contains an adhesive, such as a pressure-sensitive adhesive applied to the nonwoven substrate to allow adherence of the substrate to a person's skin. In general, any adhesive that is commonly used to adhere a substrate to human skin can be used in the present invention. In particular, an adhesive of the present invention is typically biocompatible. Moreover, in some embodiments, the adhesive is also water soluble or dispersible such that its adherent properties substantially diminish when contacted with water. For example, one preferred dispersible pressure-sensitive adhesive is HL-9415-X from H.B. Fuller Company The adhesive can generally be applied in any of a variety of amounts to the nonwoven substrate. For example, in some embodiments, the adhesive can be applied in an amount between about 3 to about 50 grams per square meter, and particularly between about 5 grams per square meter to about 25 grams per square meter.

In addition to the above-mentioned components, an adherent article of the present invention can also contain a variety of components. For instance, the adherent article can also contain an absorbent pad to aid in absorbing medicines, blood, or other fluids from a cut or wound. The absorbent pad can generally be made from any type of material. In particular, in some embodiments, the absorbent pad is dispersible in water to facilitate disposal of the article. One example of a suitable dispersible absorbent pad includes a water-dispersible coform composite material.

Moreover, the adherent article can also include a release liner that is positioned over a portion of the nonwoven substrate to cover and protect at least a portion of the pressure-sensitive adhesive. To use the adherent article, a user can simply peel away the liner from the adhesive-coated substrate and apply the substrate to the skin. In general, the release liner can be made from any commonly used material that can be peeled away from an adhesive, such as plastic films, etc.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

DETAILED DESCRIPTION OF REPRESENTATIVE EMBODIMENTS

Definitions

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes referred to as multiconstituent fibers. Fibers of this general type are discussed in, for example, U.S. Pat. Nos. 5,108,827 and 5,294,482 to Gessner. Biconstituent fibers are also discussed in the textbook *Polymer Blends and Composites* by John, A. Manson and Leslie H. Sperling, copyright 1976 by Plenum Press., a division of Plenum Publishing Corporation of New York, IBSN 0-306-30831-2, at pages 273 through 277.

"Bonded carded web" refers to webs that are made from staple fibers which are sent through a combing or carding unit, which separates or breaks apart and aligns the staple fibers to form a nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

As used herein the term "coform" generally refers to continuous melt-spun reinforcing fibers intermixed with other fibers. For example, the melt-spun fibers can be intermixed with wood pulp fibers, such as disclosed in U.S. Pat. No. 4,100,324, which is incorporated herein in its entirety by reference thereto. Moreover, the melt-spun fibers can also be intermixed with staple length fibers, such as described in U.S. Pat. No. 4,118,531, which is incorporated herein in its entirety by reference thereto. Further the melt-spun fibers, in some instances, may be intermixed with superabsorbent particulates, such as described in U.S. Pat. No. 3,971,373, which is incorporated herein in its entirety by reference thereto.

As used herein, the term "conjugate fibers" refers to fibers which have been formed from at least two polymers extruded from separated extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement, wherein one polymer is surrounded by another or may be a side-by-side arrangement, a pie arrangement or an "islands-in-the-sea" arrangement. Conjugate fibers are taught, for example, by U.S. Pat. Nos. 4,732,804; 4,115,620; and 4,068,031. For two component fibers, the polymers may be present in ratios of 75/25, 50/50, 25/75, or any other desired ratios. The fibers may also have shapes such as those described in U.S. Pat. No. 5,277,976 to Hogle et al.. U.S. Pat. No. 5,466,410 to Hill, U.S. Pat. No. 5,069,970 to Largman et al., and U.S. Pat. No. 5,057,368 to Largman et al., which describe fibers with unconventional shapes.

As used herein, the term "dispersible" refers to fibers that, after a certain period of time, will break apart into smaller pieces when placed in an aqueous solution. Thus, although dispersible fibers are not completely hydrolytically degradable, they can nevertheless be substantially disposed of in an aqueous solution.

As used herein, "meltblown fibers" refers to fibers formed by extruding a molten thermoplastic material through a plurality of fine, usually circular, die capillaries as molten threads or filaments into converging high velocity, usually hot gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous and are generally tacky when deposited on a collecting surface.

As used herein, the term "microfibers" means small diameter fibers having an average diameter not greater than about 75 micrometers, for example, having an average diameter of about 0.5 micrometers to about 50 micrometers. More particularly, microfibers may have an average diameter from about 2 micrometers to about 40 micrometers. Another frequently used expression of fiber diameter is denier, which is defined as grams per 9000 meters of a fiber and may be calculated as fiber diameter in micrometers squared, multiplied by the density in grams/cc, multiplied by 0.00707. A lower denier indicates a finer fiber and a higher denier indicates a thicker or heavier fiber. For example, the diameter of a polypropylene fiber given as 15 micrometers may be converted to denier by squaring, multiplying the result by 0.00707. Thus, a 15 micrometer polypropylene fiber has a denier of about 1.42 (15$^2$×0.89×0.00707=1.415). Outside the United States, the unit of measurement is more commonly the "tex", which is defined as the grams per kilometer of fiber. Tex may calculated as denier/9.

As used herein, the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, e.g., titanium oxide for coloration, are generally present in an amount less than about 5 weight percent and more typically about 2 weight percent.

As used herein, the term "nonwoven web" or "nonwoven substrate" refers to a web having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. The basis weight of nonwoven fabrics is usually expressed in ounces of material per square yard (osy) or grams per square meter (gsm) and the fibers diameters are usually expressed in microns. (Note that to convert from osy to gsm, multiply osy by 33.91).

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. In general, the bonding areas for thermal point bonding, whether pattern unbonded or pattern bonded fabrics, can be in the range of 50% total bond area or less. However, the percent bond areas will be affected by a number of factors, including the type(s) of polymeric materials used in forming the fibers or filaments of the nonwoven substrate, whether the nonwoven substrate is a single- or multi-layer fibrous structure, and the like. One example of a pattern has points and is the Hansen Pennings or "H&P" pattern with about a 30% bond area with about 200 bonds/square inch as taught in U.S. Pat. No. 3,855,046 to Hansen. et al.

As used herein, through air bonding or "TAB" means a process of bonding a nonwoven, for example, a bicomponent fiber web, in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provides the bonding. Through air bonding has restricted variability and is generally regarded a second step bonding process. Since TAB requires the melting of at least one component to accomplish bonding, it is restricted to webs with two components such as bicomponent fiber webs or webs containing an adhesive fiber or powder.

As used herein, "ultrasonic bonding" means a process performed, for example, by passing the fabric between a sonic horn and anvil roll as illustrated in U.S. Pat. No. 4,374,888 to Bornslaeger.

As used herein, the phrase "water soluble" generally refers to fibers that are soluble in water, as well as other aqueous solutions.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to an adherent article, such as a bandage or tape, that includes a substrate applied with a pressure sensitive adhesive, which can allow the substrate to be retained on human skin. It should be understood that an aqueous solution can include any liquid or solution, such as water or solutions thereof. It has been discovered that an adherent article of the present invention can at least partially dissolve and/or disperse in water so that a user can more easily remove the article without causing substantial pain. Moreover, it has also been discovered that an adherent article of the present invention can retain enhanced strength characteristics and dimensional integrity during use. For example in one embodiment, a substrate made from polyvinyl alcohol fibers can be applied with a pressure-sensitive hot melt adhesive to form a skin bandage that, when contacted with substantial amounts of water, dissolves and/or disperses.

In accordance with the present invention, an adherent article of the present invention includes at least one component that is soluble in water at certain temperatures. For instance, referring to FIG. 1, one embodiment of a bandage 10 is illustrated that contains a generally water soluble nonwoven substrate 12. When substantially dry, such a nonwoven substrate 12 can provide increased dimensional stability and strength to the bandage 10.

Figure 1:
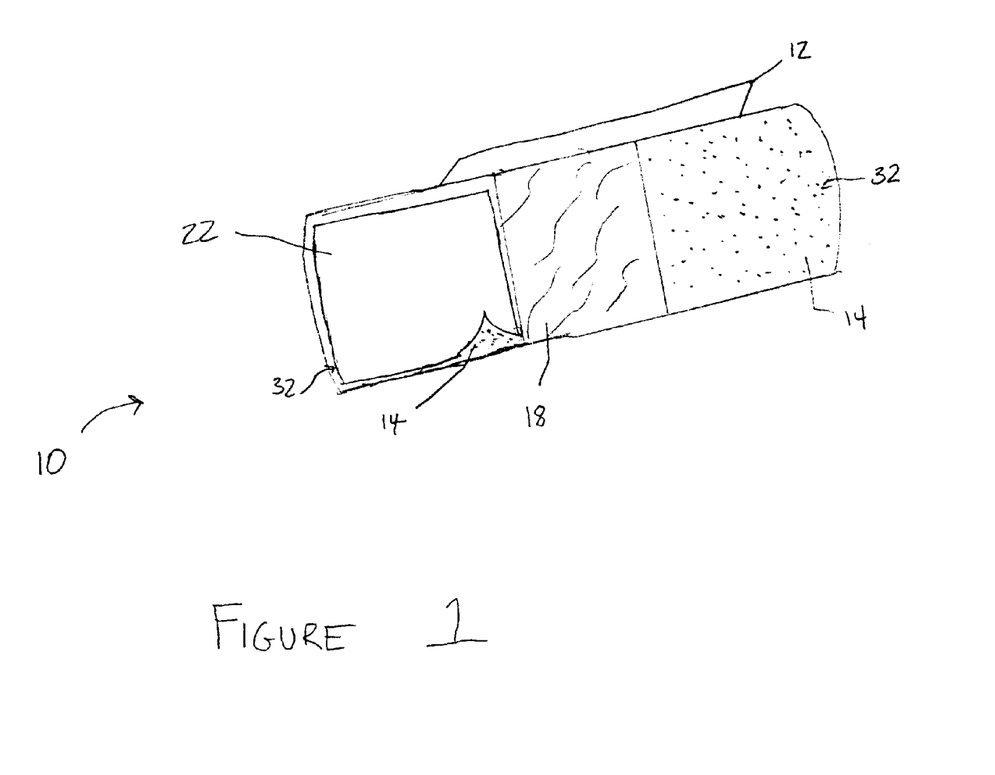
FIG. 1 is a perspective view of one embodiment of a bandage of the present invention.

In general, any material that is dissolvable in water can generally be used to form a nonwoven substrate of the present invention. For example, in some embodiments, the nonwoven substrate 12 can contain cold water soluble synthetic fibers. As used herein, "cold water soluble fibers" generally refers to fibers that can substantially dissolve in an aqueous solution at temperatures of less than about 37° C. In particular, the cold water soluble fibers of the present invention are normally capable of dissolving at temperatures between about 15° C. to about 35° C. Thus, for example, one cold water soluble fiber might dissolve at temperatures of 35° C. or higher. Another cold water soluble fiber, for example, might dissolve at temperatures of 15° C. or higher.

Any synthetic fibers that can be substantially dissolved in an aqueous solution at temperatures of less than about 37° C. can generally be used in the present invention as the cold water soluble fibers. In one embodiment, the cold water soluble fibers are polyvinyl alcohol fibers. In particular, the cold water soluble polyvinyl alcohol fibers can, in some instances, substantially dissolve in water at a temperature of at least about 20° C. to about 35° C. Commercially available polyvinyl alcohol fibers that are suitable for use as cold water soluble fibers in the present invention are Kuralon K-II fibers (Types WN2 or WJ2) staple fibers made by Kuraray Company, Ltd. (Japan). Other examples of suitable polyvinyl alcohol fibers are disclosed in U.S. Pat. No. 5,952,251 to Jackson. et al., which is incorporated herein in its entirety by reference thereto.

In addition to cold water soluble synthetic fibers, the nonwoven substrate 12 can also contain hot water soluble synthetic fibers. As used herein, "hot water soluble fibers" generally refers fibers that substantially dissolve in an aqueous solution only at temperatures greater than 37° C. For instance, in some embodiments, the hot water soluble fibers only substantially dissolve in an aqueous solution at temperatures greater than about 50° C.

Any fibers that can only be substantially dissolved in an aqueous solution at temperatures greater than 37° C. can generally be used in the present invention as the hot water soluble fibers. In one embodiment, the hot water soluble component is made from polyvinyl alcohol fibers. In one embodiment, for example, polyvinyl alcohol fibers are provided that dissolve in water at temperatures of at least 37° C. to about 50° C. One example of commercially available polyvinyl alcohol fibers that are soluble at about 50° C. are Kuralon K-II fibers (Types WN5) made by Kuraray Company, Ltd. (Japan).

Moreover, in some embodiments, the hot water soluble component can also be made from fibers that only substantially dissolve at temperatures greater than 50° C. Some examples of such fibers include VPB 201 (substantially dissolve at about 80° C. or higher) or VPB 304 (substantially dissolve at about 90° C. or higher) staple fibers made by Kuraray Company, Ltd. (Japan). Other examples of suitable polyvinyl alcohol fibers are disclosed in U.S. Pat. No. 5,207,837, which is incorporated herein in its entirety by reference thereto.

The synthetic fibers used in making the nonwoven substrate of the present invention may have any suitable morphology and may include hollow or solid, straight or crimped, single component, conjugate or biconstituent fibers or filaments, and blends or mixtures of such fibers, as are well known in the art.

In addition to synthetic fibers that are generally soluble in water at a certain temperature, the nonwoven substrate 12 can also contain other fibers that are generally insoluble, but dispersible in water. In general, any material that is dispersible and does not significantly affect the solubility of the water-soluble components within the substrate 12 can be utilized in accordance with the present invention. In one embodiment, pulp fibers can be utilized. For instance, the pulp fibers can be softwood fibers having an average fiber length of greater than 1 mm and particularly from about 2 to 5 mm based on a length-weighted average. Such fibers can include Northern softwood kraft fibers, redwood fibers, pine fibers, spruce fibers, or a combination thereof. Secondary fibers obtained from recycled materials may also be used.

In addition, staple fibers can also be added to the nonwoven substrate 12 to increase the strength, bulk, softness and smoothness of the substrate. As used herein, the term "staple fiber" is meant to refer to a natural fiber or a length cut from, for example, a manufactured filament. The staple fibers used in the nonwoven substrate can, for example, range in fiber length from about 0.1 to about 15 cm, and particularly from about 0.2 to about 7 cm. For instance, some examples of suitable staple fibers can include, various polyolefin fibers, polyester fibers, nylon fibers, polyvinyl acetate fibers, cotton fibers, rayon fibers, non-woody plant fibers, and mixtures thereof. In particular, one preferred type of rayon staple fibers can be obtained commercially from Courtaulds Coatings (Holdings) Limited (GB).

Regardless of the fibers utilized, the nonwoven substrate 12 generally contains water soluble fibers, whether hot water soluble or cold water soluble, in an amount of at least about 50% by weight of the substrate. In particular, the nonwoven substrate 12 can contain at least about 70% by weight of water-soluble fibers, and more particularly, at least about 80% by weight of water-soluble fibers. For example, in one embodiment, the nonwoven substrate 12 contains about 100% cold water soluble polyvinyl alcohol fibers. In another embodiment, the nonwoven substrate 12 contains about 50% cold water soluble polyvinyl alcohol fibers and 50% hot water soluble fibers. Moreover, in yet another embodiment, the nonwoven substrate 12 contains about 50% cold water soluble polyvinyl alcohol fibers and 50% rayon fibers.

In general, the nonwoven substrate 12 can be formed into a web using any technique known in the art for making nonwoven webs. Such nonwoven techniques useful for making polymer sheets include spunbonding, meltblowing, wet-laying, carding, etc.

For example, in one embodiment, the nonwoven substrate 12 is formed through a bonded carded process as is well-known in the art. For example, a web of water-soluble polyvinyl alcohol fibers may be formed by carding the fibers into a web. Although not required, the fibers can also be cross-layed (cross-lapped) in the machine direction and/or cross machine direction and thereafter thermal point bonded to achieve further strength. In one embodiment, the web of polyvinyl alcohol fibers has a basis weight less than about 70 grams per square meter, and particularly less than about 55 grams per square meter, and more particularly less than about 40 grams per square meter.

Various methods may be utilized in bonding webs of the present invention. Such methods include through-air bonding and thermal point bonding, such as described in U.S. Pat. No. 3,855,046 to Hansen et al, which is incorporated in its entirety herein by reference thereto. In addition, other means of bonding, such as ultrasonic bonding, hydroentangling, etc., may be utilized in certain instances, such as when using only hot water soluble fibers. Hydroentangling may be accomplished utilizing conventional hydroentangling equipment such as may be found in, for example, in U.S. Pat. No. 3,485,706 to Evans or U.S. Pat. No. 5,389,202 to Everhart et al., which are incorporated herein in their entirety by reference thereto.

In order to facilitate adhesion of the nonwoven substrate 12 to a person's skin, an adhesive can be applied to the substrate. Although not required, in most embodiments, the adhesive is a pressure-sensitive adhesive. A pressure sensitive adhesive is an adhesive that is normally tacky at room temperature (e.g., about 20° C.) and that can form a bond to a surface by the application of small amounts of pressure.

In general, any of a variety of pressure-sensitive adhesives can be utilized in the present invention. In particular, pressure-sensitive adhesives that are biocompatible with human skin are typically utilized. Moreover, an adhesive of the present invention is also either generally water soluble or generally insoluble, but dispersible in an aqueous environment. For instance, one preferred, commercially available dispersible pressure-sensitive adhesive is sold under the trade name of HL-9415-X and is available from H.B. Fuller Company. Other suitable water soluble or generally insoluble, but dispersible, pressure-sensitive adhesives are described in U.S. Pat. No. 4,990,339 to Scholl, et al.; U.S. Pat. No. 5,512,615 to Brown. et al.; U.S. Pat. No. 5,599,872 to Sulewski; U.S. Pat. No. 5,641,567to Brown, et al.; and U.S. Pat. No. 5,952,420 to Senkus. et al., which are incorporated herein in their entirety by reference thereto. For example, one suitable adhesive disclosed in Scholl. et al. includes about 10–75% by weight of a polyalkyloxazoline polymer, 10–75% by weight of a functional diluent comprising a hydroxy compound or a carboxylic acid compound, and 5–50% by weight of a tackifier.

Moreover, one suitable adhesive disclosed in Brown, et al. includes a polymeric, solvent-insoluble, solvent-dispersible microparticles and a water-dispersible polymeric component. The water-dispersible polymeric component can include, for example, surfactants such as poly(ethylene oxide) alkylphenyl ethers, such as those sold under the name IGEPAL®.CO and IGEPAL®.CA (available from Rhone-Poulenc, Inc.); poly(ethylene oxide) lauryl, cetyl, and oleyl ethers such as those sold under the name Brij® (available from ICI Americas, Inc.); poly(ethylene oxide) laurate;

poly(ethylene oxide) oleate; sorbitan oleate; ethylene oxide/ propylene oxide block copolymers such as those sold under the name PLURONIC® and TETRONIC® (available from BASF Corporation); and organic phosphate esters, such as Gafac®) PE-510 (available from International Specialty Products). Other water-dispersible polymers useful in the pressure-sensitive adhesive of the present invention include those disclosed in U.S. Pat. Nos. 2,838,421, 3,441,430, 4,442,258, 3,890,292, and 5,196,504, and DE-C 23 11 76. Examples of such components include, but are riot limited to, poly(acrylic acid); poly(vinyl alcohol); poly(N-vinyl pyrrolidone); poly(acrylamide); poly(alkoxyalkyl (meth) acrylates), such as 2-ethoxy ethyl acrylate, 2-ethoxy ethyl methacrylate, 2-(2-ethoxyethoxy) ethyl acrylate, and 2-methoxy ethyl acrylate (available from SARTOMER Company, Inc.); poly(vinyl methyl ether); poly(vinyl methyl ether: maleic anhydride), sold under the name "GANTREZ" (available from International Specialty Products); poly(ether polyols), such as poly(propylene glycol) and the like, such as those sold under the name "SANNIX" (available from Sanyo Chemical Industries); copolymers thereof, and the like. Copolymers of these and alkyl (meth)acrylate esters or vinyl esters are also suitable. Gums such as those derived from okra and guar may also be used.

Still other suitable pressure-sensitive adhesives are described in U.S. Pat. No. 4,033,918 to Hauber and U.S. Pat. No. 5,527,844 to Strelow. et al., and EP 0554106 A1, which are incorporated herein in their entirety by reference thereto. One such adhesive disclosed in Strelow includes about 10% to about 80%, by weight, of an alkali soluble polymer; about 0 to about 30%, by weight, of a poly(vinyl methyl ether); about 30% to about 70%, by weight, of a tackifying resin; and about 5% to about 30%, by weight, of a suitable plasticizer. Still other examples of suitable adhesives include HX 9236-01 or HX 9237-01 hot melt adhesives, which are obtainable from ATO Findley, Inc..

In general, as stated above, the pressure-sensitive adhesive 14 can be applied to one or both sides of the substrate 12. For instance, as shown in FIG. 1, the pressure-sensitive adhesive 14 is applied only to the side of the substrate 12 that is designed to adhere to human skin. The pressure-sensitive adhesive 14 can generally be applied to the nonwoven substrate 12 through any known method of application, such as print, film, spray, saturant, coat, droplet throw, and foam applications. In one embodiment, for example, the adhesive 14 can be sprayed onto the nonwoven substrate 12 using a melt spray applicator, such as available from J. & M. Laboratories Inc., believed to be described in U.S. Pat. No. 5,728,219, which is incorporated herein in its entirety by reference thereto. Moreover, in another embodiment, the adhesive 14 can be applied as a film layer to the nonwoven substrate 12, such as described in U.S. Pat. No. 4,990,339 to Scholl. et al.

In addition, depending on the desired adherent characteristics of the resulting article, the pressure-sensitive adhesive 14 can be applied in any of a variety of amounts to the substrate 12. For example, in some embodiments, the pressure-sensitive adhesive 14 can be applied in an amount between about 3 grams per square meter (GSM) to about 50 grams per square meter, and particularly between about 5 grams per square meter to about 25 grams per square meter. Further, the adhesive 14 can also be applied either uniformly or non-uniformly to one or both sides of the substrate 12. For example, as illustrated in FIG. 1, the adhesive 14 can be applied to only the outer regions 32 of the substrate 12 to further facilitate removal of the substrate 12 from a person's skin without causing substantial pain.

As a result of the present invention, the bandage 10 can generally be removed from a person's skin by using an aqueous solution, such as water from a shower, bath, faucet, etc. For example, when the bandage 10 contacts a sufficient amount of water, the water-soluble fibers within the substrate 12 substantially dissolve as described above. Consequently, any dispersible fibers or materials contained within the substrate 12 can then disperse into smaller pieces and be flushed down a drain or sink for easy disposal. Moreover, the same water can also cause the pressure-sensitive adhesive 14 of the bandage 10 to disperse and lose its strength and adherent properties, thereby allowing the bandage 10 to be even more easily removed.

Although not required, the bandage 10 can also contain a variety of other components. For instance, as shown in FIG. 1, the bandage 10 can also contain an absorbent pad 18 to aid in absorbing or delivering medicines and/or absorbing blood or fluids from a cut or wound. The absorbent pad 18 can generally be made from any type of material commonly used in the art in forming such pads. In some embodiments, the absorbent pad 18 can also be dispersible in water to facilitate in disposal of the bandage 10. For example, water-dispersible coform composites are one example of a suitable absorbent pad that can be used in the present invention. Some examples of such water-dispersible coform composites are described in U.S. Pat. No. 5,952,251 to Jackson, et al. and U.S. Pat. No. 5,948,710 to Pomplun. et al., which are incorporated herein in their entirety by reference thereto. Other suitable materials that can be used for the absorbent pad 18 include lightly cross-linked tissue structures, absorbent films, and the like.

Moreover, as shown, the bandage 10 can also include a release liner 22 that is positioned over a portion of the substrate 12 to cover the pressure-sensitive adhesive 14. By covering the pressure-adhesive 14, the release liner 22 can ensure that the adherent properties of the adhesive 14 remain in tact until utilized. To use the bandage 10, a user can simply peel away the liner 22 and adhere the substrate 12 to the skin at by contacting the adhesive portions of the substrate 12 to the skin. In general, the release liner 22 can be made from any material commonly used in the art as a liner for an adhesive bandage. For example, some suitable release liners are described in U.S. Pat. Nos. 5,643,188 to Oliveira and U.S. Pat. No. 5,947,917 to Carte. et al., which are incorporated herein in their entirety by reference thereto. Moreover, although not required, the release liner 22 may be generally dispersible in water, such as described above, to further enhance waste disposal.

In addition to the above components, other chemicals and/or additives can also be employed in forming an adherent article of the present invention. In general, any chemical that does not significantly affect the solubility and/or dispersibility of fibers within an article of the present invention can be added. For instance, in one embodiment, anionic or cationic dyes can be used to impart a particular color to the resulting adherent article.

The present invention may be better understood with reference to the following examples.

EXAMPLE 1

The ability of a bandage of the present invention to be dispersed with water was demonstrated. Various samples of bonded carded webs were made from water soluble polyvinyl alcohol (PVA) staple fibers. Two types of polyvinyl alcohol fibers were used as the water soluble fibers for the samples, i.e., one being soluble in water at a temperature of at least 20° C. (Kuralon K-II staple fibers, WJ2, 2.2 dtex in average diameter, and 51 mm in average length), the other being soluble in water at a temperature of at least 50° C. (Kuralon K-II staple fibers, WN5, 1.5 dtex in average diameter, and 55 mm in average length). Rayon staple fibers (1.5 dtex in average diameter and 40 mm in average length) from Courtaulds Coatings (Holdings) Limited (GB) were also utilized in some of the web samples.

The carded webs were thermally bonded via a single nip calendering system consisting of a steel pattern roll against a steel anvil roll. The pattern roll had a repeating, uniformly spaced arrangement of pin elements, with each pin element having a surface area of about 0.0005 to 0.00086 inches squared, to produce a total bond area of about 25% of the fabric surface area. The temperatures of steel rolls were set between 250° F. and 330° F. Moreover, the basis weights of the samples varied from 34.8 grams per square meter to 43.7 grams per square meter. The characteristics of the samples are given below in Table 1 below.

A pressure-sensitive, hot melt adhesive, either in film or meltspray form, was also attached to one side of each sample web. The hot melt adhesive was HL-9415-X from HB Fuller. The adhesive was dispersible in water and is believed to be related to the formulations described in HB fuller's U.S. Pat. No. 4,990,339 to Scholl. et al.. The form of the adhesive and the amount attached to the nonwoven webs are listed below in Table 1.

TABLE 1

Sample Characteristics

| Sample | Cold-Water PVA (wt. %) (WJ2) | Hot-Water PVA (wt. %) (WN5) | Rayon (wt. %) | Adhesive Amount (GSM) | Adhesive Form |
|---|---|---|---|---|---|
| 1  | 50  | 50  | 0  | 17 | Film |
| 2  | 0   | 100 | 0  | 17 | Film |
| 3  | 50  | 50  | 0  | 23 | Film |
| 4  | 0   | 100 | 0  | 23 | Film |
| 5  | 50  | 50  | 0  | 5  | Meltspray |
| 6  | 100 | 0   | 0  | 5  | Meltspray |
| 7  | 100 | 0   | 0  | 10 | Meltspray |
| 8  | 50  | 0   | 50 | 5  | Meltspray |
| 9  | 50  | 0   | 50 | 10 | Meltspray |
| 10 | 50  | 50  | 0  | 10 | Meltspray |
| 11 | 50  | 0   | 50 | 5  | Meltspray |
| 12 | 0   | 100 | 0  | 10 | Meltspray |
| 13 | 0   | 50  | 50 | 10 | Meltspray |
| 14 | 0   | 100 | 0  | 5  | Meltspray |

The carded webs were then cut into 1"×3" strips for evaluations via immersion in water. The strips were adhered to 1"×3" glass slides and completely immersed for 30 minutes in containers containing 1 9° C. water (~200 ml). Thereafter, each container was inverted 3 times within 8 minutes to impart a degree of agitation. Changes were observed in the strips as "distorted", "shrunk", "distorted and shrunk", or "adhered".

"Distorted" meant that the rectangular strip partially dispersed and fragmented into an irregularly shaped structure, i.e., having no resemblance to a rectangle.

"Shrunk" meant the structure retained its rectangular dimensions, but the dimensions decreased by at least 50%.

"Distorted & Shrunk" meant the initial rectangular structure changed to an irregular structure and the nonwoven web appeared to shrink to a slight degree.

"Adhered" meant that the strip remained attached to the glass slide.

The observations of changes in the strips after immersion are given below in Table 2:

TABLE 2

Sample Observations

| Sample | Observation |
|---|---|
| 1  | Distorted and Shrunk |
| 2  | Shrunk |
| 3  | Shrunk |
| 4  | Shrunk |
| 5  | Adhered |
| 6  | Distorted |
| 7  | Distorted |
| 8  | Distorted |
| 9  | Distorted |
| 10 | Distorted and Shrunk |
| 11 | Distorted and Shrunk |
| 12 | Shrunk |
| 13 | Shrunk |
| 14 | Shrunk |

As indicated above, all the strips, except one (Sample #5), detached from the glass slides and changed their form after immersion.

EXAMPLE 2

The ability of a bandage of the present invention to be dispersed with substantial amounts of water was demonstrated. The bonded carded webs containing 100% cold water soluble PVA fibers (i.e., WJ2) of Example 1 were utilized to form various bandage samples. A coating of the HL-9415-X from HB Fuller having a thickness of about 0.001 inches was applied to each web.

After forming the webs, comparative samples were also prepared utilizing commercial bandages called ARcare® 8115 from Adhesives Research, Inc. The comparative samples contained a spunlace nonwoven web made from polyester staple fibers and a proprietary adhesive coating, ON/OFF® (MA-48) also from Adhesives Research, Inc. The adhesive is believed to be of the type described in EP 0554106 A1.

The webs were then cut. into 1"×3" strips for evaluations via immersion in water. The strips were adhered to 1"×3" glass slides and these were placed in containers and completely immersed in 19° C. water (~200 ml) for 14 hours. Thereafter, each container was inverted 3 times within 8 minutes to impart a degree of agitation. As described in Example 1, changes were observed in the strips as either "adhered", "dispersed", or "detached, but same shape". "Dispersed" includes the characteristics of shrunk, distorted, or distorted and shrunk, as described above. "Detached, but same shape" refers to the observation that a strip detaches from the slide, but retained substantially the same shape.

TABLE 3

Sample Results

| Bandage Type | Dry Weight (gm) | Post-Immersion Form |
|---|---|---|
| ARcare ® 8115 | 0.304 | Detached, same shape |
| ARcare ® 8115 | 0.297 | Detached, same shape |
| 100% Cold-Water Soluble PVA w/HL-9415-X | 0.310 | Dispersed |
| 100% Cold-Water Soluble PVA w/HL-9415-X | 0.301 | Dispersed |

The ARcare® strips retained 95% or more of their original weight after being dried. The adhesiveness of the ARcare® strips returned once the strips were dried. On the other hand, the strips made from the cold water soluble polyvinyl alcohol staple fibers with the HL-9415-X adhesive in accordance with the present invention lost all structural integrity. The residual weights remaining on the glass slides after drying were less than 2% of the original weight.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An adherent article comprising:
   a nonwoven substrate having a first and second side, said nonwoven substrate comprising fibers that are soluble in an aqueous solution selected from the group consisting of cold water soluble fibers, hot water soluble fibers, and combinations thereof, wherein said fibers soluble in said aqueous solution comprise greater than about 50% by weight of said nonwoven substrate; and
   an adhesive applied to at least a portion of said first side of said nonwoven substrate, said adhesive being capable of adhering said nonwoven substrate to human skin in the absence of said aqueous solution.

2. An adherent article as defined in claim 1, wherein said nonwoven substrate comprises cold water soluble fibers.

3. An adherent article as defined in claim 2, wherein said cold water soluble fibers comprise polyvinyl alcohol fibers.

4. An adherent article as defined in claim 1, wherein said nonwoven substrate comprises hot water soluble fibers.

5. An adherent article as defined in claim 4, wherein said hot water soluble fibers comprise polyvinyl alcohol fibers.

6. An adherent article as defined in claim 2, further comprising hot water soluble fibers.

7. An adherent article as defined in claim 1, wherein said nonwoven substrate further comprises fibers that are generally non-soluble and dispersible in said aqueous solutions.

8. An adherent article as defined in claim 7, wherein said dispersible fibers comprise less than about 50% by weight of said nonwoven substrate.

9. An adherent article as defined in claim 7, wherein said dispersible fibers comprise pulp fibers.

10. An adherent article as defined in claim 7, wherein said dispersible fibers comprise staple fibers.

11. An adherent article as defined in claim 10, wherein said staple fibers comprise rayon fibers.

12. An adherent article as defined in claim 1, wherein said adhesive comprises a pressure-sensitive adhesive that is generally non-soluble and dispersible in said aqueous solution.

13. An adherent article as defined in claim 1, wherein said adhesive is soluble in said aqueous solution.

14. An adherent article as defined in claim 1, further comprising an absorbent pad attached to said first side of said nonwoven substrate.

15. An adherent article as defined in claim 1, further comprising a release liner, said release liner being positioned on said nonwoven substrate such that said release liner substantially covers said adhesive.

16. An adherent article comprising:
    a nonwoven substrate having a first and second side, said nonwoven substrate comprising polyvinyl alcohol fibers that are soluble in an aqueous solution selected from the group consisting of cold water soluble polyvinyl alcohol fibers, hot water soluble polyvinyl alcohol fibers, and combinations thereof, said polyvinyl alcohol fibers comprising greater than about 50% by weight of said nonwoven substrate; and
    a pressure-sensitive adhesive applied to at least a portion of said first side of said nonwoven substrate, said pressure-sensitive adhesive being capable of adhering said nonwoven substrate to human skin in the absence of said aqueous solution, said pressure-sensitive adhesive being either soluble in said aqueous solution or generally non-soluble, and dispersible in said aqueous solution.

17. An adherent article as defined in claim 16, wherein said polyvinyl alcohol fibers are cold water soluble fibers.

18. An adherent article as defined claim 17, further comprising hot water soluble polyvinyl alcohol fibers.

19. An adherent article as defined in claim 16, wherein said polyvinyl alcohol fibers are hot water soluble.

20. An adherent article as defined in claim 16, wherein said nonwoven substrate further comprises fibers that are generally non-soluble and dispersible in said aqueous solution.

21. An adherent article as defined in claim 20, wherein said dispersible fibers comprise less than about 50% by weight of said nonwoven substrate.

22. An adherent article as defined in claim 20, wherein said dispersible fibers comprise pulp fibers.

23. An adherent article as defined in claim 20, wherein said dispersible fibers comprise staple fibers.

24. An adherent article as defined in claim 16, further comprising an absorbent pad attached to said first side of said nonwoven substrate.

25. An adherent article as defined in claim 16, further comprising a release liner, said release liner being positioned on said nonwoven substrate such that said release liner substantially covers said pressure-sensitive adhesive.

26. A bandage comprising:
    a nonwoven substrate having a first and second side, said nonwoven substrate comprising polyvinyl alcohol fibers that are soluble in an aqueous solution selected from the group consisting of cold water soluble polyvinyl alcohol fibers, hot water soluble polyvinyl alcohol fibers, and combinations thereof, wherein said polyvinyl alcohol fibers comprise greater than about 50% by weight of said nonwoven substrate; and
    a pressure-sensitive adhesive applied to at least a portion of said first side of said nonwoven substrate, said pressure-sensitive adhesive being capable of adhering said nonwoven substrate to human skin in the absence of said aqueous solution, said pressure-sensitive adhesive being either soluble in said aqueous solution or generally non-soluble and dispersible in said aqueous solution; and
    an absorbent pad attached to said first side of said nonwoven substrate.

27. A bandage as defined in claim 26, wherein said absorbent pad comprises fibers that are generally non-soluble and dispersible in said aqueous solution.

28. A bandage as defined in claim 26, further comprising a release liner, said release liner being positioned on said nonwoven substrate such that said release liner substantially covers said pressure-sensitive adhesive.

29. A bandage as defined in claim 26, wherein said polyvinyl alcohol fibers are cold water soluble fibers.

30. A bandage as defined claim 29, further comprising hot water soluble polyvinyl alcohol fibers.

31. A bandage as defined claim 26, wherein said polyvinyl alcohol fibers are hot water soluble fibers.

32. A bandage as defined in claim 26, wherein said nonwoven substrate further comprises fibers that are generally non-soluble and dispersible in said aqueous solution.

33. An adherent article comprising:
a nonwoven substrate having a first and second side, said nonwoven substrate comprising cold water soluble fibers and hot water soluble fibers; and
an adhesive applied to at least a portion of said first side of said nonwoven substrate, said adhesive being capable of adhering said nonwoven substrate to human skin in the absence of said aqueous solution.

34. An adherent article as defined in claim 33, wherein said cold water soluble fibers comprise polyvinyl alcohol fibers.

35. An adherent article as defined in claim 33, wherein said hot water soluble fibers comprise polyvinyl alcohol fibers.

36. An adherent article as defined in claim 33, wherein said cold water soluble fibers and hot water soluble fibers comprise at least about 50% by weight of said nonwoven substrate.

37. An adherent article as defined in claim 33, wherein said nonwoven substrate further comprises fibers that are generally non-soluble and dispersible in said aqueous solution.

38. An adherent article as defined in claim wherein said dispersible fibers comprises less than about 50% by weight of said nonwoven substrate.

39. An adherent article as defined in claim 37, wherein said dispersible fibers comprise pulp fibers, staple fibers, or combinations thereof.

40. An adherent article as defined in claim 33, wherein said adhesive comprises a pressure-sensitive adhesive that is generally non-soluble and dispersible in said aqueous solution.

41. An adherent article as defined in claim 33, wherein said adhesive comprises a pressure-sensitive adhesive that is soluble in said aqueous solution.

42. An adherent article as defined in claim 33, further comprising an absorbent pad attached to said first side of said nonwoven substrate.

43. An adherent article as defined in claim 33, further comprising a release liner, said release liner being positioned on said nonwoven substrate such that said release liner substantially covers said adhesive.

44. An adherent article comprising:
a nonwoven substrate having a first and second side, said nonwoven substrate comprising polyvinyl alcohol fibers that are soluble in an aqueous solution, said polyvinyl alcohol fibers comprising hot water soluble polyvinyl alcohol fibers and cold water soluble polyvinyl alcohol fibers, said polyvinyl alcohol fibers comprising greater than about 50% by weight of said nonwoven substrate; and
a pressure-sensitive adhesive applied to at least a portion of said first side of said nonwoven substrate, said pressure-sensitive adhesive being capable of adhering said nonwoven substrate to human skin in the absence of said aqueous solution, said pressure-sensitive adhesive being either soluble in said aqueous solution or generally non-soluble and dispersible in said aqueous solution.

45. A bandage comprising:
a nonwoven substrate having a first and second side, said nonwoven substrate comprising polyvinyl alcohol fibers that are soluble in an aqueous solution, said polyvinyl alcohol fibers comprising hot water soluble polyvinyl alcohol fibers and cold water soluble polyvinyl alcohol fibers; and
a pressure-sensitive adhesive applied to at least a portion of said first side of said nonwoven substrate, said pressure-sensitive adhesive being capable of adhering said nonwoven substrate to human skin in the absence of said aqueous solution, said pressure-sensitive adhesive being either soluble in said aqueous solution or generally non-soluble and dispersible in said aqueous solution; and
an absorbent pad attached to said first side of said nonwoven substrate.

\* \* \* \* \*

UNITED STATES PATENT AND TRADEMARK OFFICE
CERTIFICATE OF CORRECTION

PATENT NO. : 6,576,575 B2
DATED : June 10, 2003
INVENTOR(S) : Henry L. Griesbach, III and Julie R. Taylor It is certified that error appears in the above-identified patent and that said Letters Patent is hereby corrected as shown below:

<u>Column 15,</u>
Line 28, after "claim" add -- 37 --.

Signed and Sealed this

Thirtieth Day of December, 2003

JAMES E. ROGAN
*Director of the United States Patent and Trademark Office*